United States Patent
Cesco-Cancian et al.

(10) Patent No.: US 8,748,396 B2
(45) Date of Patent: *Jun. 10, 2014

(54) LYOPHILIZATION OF SYNTHETIC LIPOSOMAL PULMONARY SURFACTANT

(71) Applicant: Discovery Laboratories, Inc., Warrington, PA (US)

(72) Inventors: Sergio Cesco-Cancian, Bethlehem, PA (US); Thomas Hoy, Pipersville, PA (US); Edward H. Trappler, Langhorne, PA (US); Michael S. Thomas, Holland, PA (US)

(73) Assignee: Discovery Laboratories, Inc., Warrington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/091,608

(22) Filed: Nov. 27, 2013

(65) Prior Publication Data

US 2014/0088025 A1 Mar. 27, 2014

Related U.S. Application Data

(63) Continuation of application No. PCT/US2013/034364, filed on Mar. 28, 2013.

(60) Provisional application No. 61/616,827, filed on Mar. 28, 2012.

(51) Int. Cl.
*A61K 9/19* (2006.01)
*C07K 14/785* (2006.01)
*A61K 31/685* (2006.01)
*A61K 31/20* (2006.01)
*A61K 31/683* (2006.01)
*A61K 38/17* (2006.01)

(52) U.S. Cl.
CPC .......... *A61K 9/19* (2013.01); *A61K 38/395* (2013.01); *C07K 14/785* (2013.01); *A61K 31/685* (2013.01); *A61K 31/20* (2013.01); *A61K 31/683* (2013.01)
USPC ............................................. 514/21.4

(58) Field of Classification Search
CPC ....... A61K 9/19; A61K 38/395; C07K 14/785
See application file for complete search history.

(56) References Cited

U.S. PATENT DOCUMENTS

| | | |
|---|---|---|
| 5,789,381 A | 8/1998 | Cochrane et al. |
| 5,952,303 A | 9/1999 | Bornstein et al. |
| 7,582,312 B2 | 9/2009 | Johnson et al. |

FOREIGN PATENT DOCUMENTS

WO     WO 92/22315 A1    12/1992

OTHER PUBLICATIONS

Hopp et al., "Prediction of Protein Antigenic Determinants From Amino", Proc. Natl. Acad. Sci. 78: 3824-3829, 1981.
Corresponding International Search Report and Written Opinion Application No. PCT/US2013/034364, mailed Jul. 18, 2013.
Corresponding International Search Report and Written Opinion Application No. PCT/US2013/034464, mailed Aug. 6, 2013.

*Primary Examiner* — Christina Bradley
(74) *Attorney, Agent, or Firm* — Potter Anderson and Corroon LLP

(57) ABSTRACT

Lyophilized pulmonary surfactants having an increased specific surface area and porosity are described. A method of making lyophilized pulmonary surfactants is described.

12 Claims, 6 Drawing Sheets

SEQUENCE LISTING

```
<160> NUMBER OF SEQ ID NOS: 13

<210> SEQ ID NO 1
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 1

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 2
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 2

Asp Leu Leu Leu Leu Asp Leu Leu Leu Leu Asp Leu Leu Leu Leu Asp
1               5                   10                  15

Leu Leu Leu Leu Asp
            20

<210> SEQ ID NO 3
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
```

```
                                  Sequence)

<400> SEQUENCE: 3

Arg Leu Leu Leu Leu Arg Leu Leu Leu Arg Leu Leu Leu Leu Arg
1               5                   10                  15

Leu Leu Leu Leu Arg
            20

<210> SEQ ID NO 4
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 4

Arg Leu Leu Leu Leu Leu Leu Leu Arg Leu Leu Leu Leu Leu Leu
1               5                   10                  15

Leu Leu Arg Leu Leu
            20

<210> SEQ ID NO 5
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 5

Arg Arg Leu Leu Leu Leu Leu Leu Leu Arg Arg Leu Leu Leu Leu
1               5                   10                  15

Leu Leu Arg Arg Leu
            20

<210> SEQ ID NO 6
<211> LENGTH: 20
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 6

Arg Leu Leu Leu Leu Cys Leu Leu Arg Leu Leu Leu Leu Leu Cys
1               5                   10                  15

Leu Leu Leu Arg
            20

<210> SEQ ID NO 7
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 7

Leu Leu Leu Leu Leu Cys Leu Leu Leu Arg Leu Leu Leu Leu Cys Leu
1               5                   10                  15

Leu Leu Arg Leu Leu
            20

<210> SEQ ID NO 8
```

```
<211> LENGTH: 49
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 8

Arg Leu Leu Leu Leu Cys Leu Leu Arg Leu Leu Leu Leu Cys Leu
1               5                   10                  15

Leu Leu Arg Leu Leu Leu Leu Cys Leu Leu Arg Asp Leu Leu Leu
            20                  25                  30

Asp Leu Leu Leu Asp Leu Leu Leu Asp Leu Leu Leu Asp Leu Leu Leu
        35                  40                  45

Asp

<210> SEQ ID NO 9
<211> LENGTH: 19
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 9

Arg Leu Leu Leu Leu Cys Leu Leu Arg Leu Leu Leu Leu Cys Leu
1               5                   10                  15

Leu Leu Arg

<210> SEQ ID NO 10
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 10

Arg Leu Leu Leu Leu Cys Leu Leu Arg Leu Leu Leu Leu Cys Leu
1               5                   10                  15

Leu Leu Arg Leu Leu
            20

<210> SEQ ID NO 11
<211> LENGTH: 28
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 11

Arg Leu Leu Leu Leu Cys Leu Leu Arg Leu Leu Leu Leu Cys Leu
1               5                   10                  15

Leu Leu Arg Leu Leu Leu Leu Cys Leu Leu Leu Arg
            20                  25

<210> SEQ ID NO 12
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 12
```

-continued

```
Lys Leu Leu Leu Leu Leu Leu Leu Leu Lys Leu Leu Leu Leu Leu Leu
1               5                   10                  15

Leu Leu Lys Leu Leu
            20

<210> SEQ ID NO 13
<211> LENGTH: 21
<212> TYPE: PRT
<213> ORGANISM: Artificial Sequence
<220> FEATURE:
<223> OTHER INFORMATION: Pulmonary Surfactant Mimetic Peptide (Synthetic
      Sequence)

<400> SEQUENCE: 13

Lys Lys Leu Leu Leu Leu Leu Leu Leu Lys Lys Leu Leu Leu Leu Leu
1               5                   10                  15

Leu Leu Lys Lys Leu
            20
```

LYOPHILIZATION OF SYNTHETIC LIPOSOMAL PULMONARY SURFACTANT

CROSS-REFERENCE TO RELATED APPLICATIONS

Continuation of PCT/US2013/034364, filed Mar. 28, 2013, which claims benefit of the filing date of U.S. Provisional Application No. 61/616,827, filed Mar. 28, 2012, the entire contents of each of which are incorporated by reference herein.

BACKGROUND OF THE INVENTION

1. Field of Invention

This invention relates to a solid synthetic pulmonary surfactant and a method of manufacturing thereof.

2. Description of Related Art

Pulmonary surfactant (also referred to as "lung surfactant") is a complex mixture of lipids and proteins that promotes the formation of a monolayer at the alveolar air-water interface, and by reducing the surface tension, prevents the collapse of the alveolus during expiration. Lung surfactant lines the alveolar epithelium of mature mammalian lungs. Natural lung surfactant has been described as a "lipoprotein complex" because it contains both phospholipids and apoproteins that interact to reduce surface tension at the lung air-liquid interface. Four proteins have been found to be associated with lung surfactant, namely SP-A, SP-B, SP-C, and SP-D. Specifically, SP-B appears to be essential for the biophysical action of lung surfactant. It is accepted therapy for the treatment of a variety of respiratory disorders to administer lung surfactant to the patient's lungs.

From a pharmacological point of view, the optimal exogenous lung surfactant to use in the treatment would be completely synthesized in the laboratory. In this regard, one mimetic of SP-B that has found to be useful is KL4, which is a 21 amino acid cationic polypeptide.

One method of manufacturing lung surfactant on a commercial-scale for medical use is by a process that utilizes a thin film evaporator (TFE) unit operation. The process as it applies to the production of KL4 lung surfactant consists of the following steps: 1) solubilizing the four primary formulation components, dipalmitoyl phosphatidylcholine (DPPC), palmitoyloleoyl phosphatidylglycerol (POPG) and palmitic acid (PA) and KL4 in ethanol; 2) removing the ethanol utilizing the TFE; and 3) dispensing the final dispersion into vials. The TFE unit operation itself is complex and has scaling limitations. Specifically, a 1 ft$^2$ TFE produces a 40-liter batch and the biggest comparable unit available is a 10 ft$^2$ TFE. This restricts the batch size, which is undesirable as additional indications are approved for the KL4 surfactant requiring ever increasing amounts of surfactant. Moreover, the process is performed under aseptic conditions that contribute significantly to the cost, scheduling flexibility, and complexity of the product.

In addition to the cost and complexity of using a TFE, a further complication exists due to the composition being stored in a liquid state. Because the polypeptide and lipid components of the composition are subject to degradation, the solution must be kept refrigerated to retard any degradation and achieve long term stability.

Lyophilization or freeze-drying is an important process in manufacturing solid pharmaceutical formulations. Solid formulations have longer stability than liquid formulations and are easier to transport and store. During the lyophilization process, a pharmaceutical formulation can be dried to 2% or less of residual moisture content without raising a temperature above 30° C. Therefore, this process is less likely to cause thermal degradation of formulations than a high temperature process such as, for example, spray drying.

The lyophilization process involves freezing a liquid formulation and removing the solvent associated with it by direct sublimation from the solid phase to the vapor phase without passing through the intermediate liquid phase. Generally, the lyophilization process consists of three stages, freezing stage, primary drying, and secondary drying.

Freezing is the process of solidification of a starting liquid by means of cooling the material below a given temperature less than or equal to 0° C. Primary drying is the portion of the lyophilization cycle in which sublimation of a majority of the frozen solvents are removed while the material is kept below a threshold temperature in order to maintain the structure established during the freeze. Secondary drying is the process of desorption of a portion of the residual moisture and is usually conducted at temperatures of 25° C. and above. The critical process parameters associated with each of these three steps are shelf temperature, chamber pressure and time.

Lyophilization process continues to evolve through decades. Despite ample knowledge developed in this area, the challenges of producing a uniformly distributed cake having mechanically stable structure on a commercial scale at a reasonable cost and time remain.

U.S. Pat. No. 5,952,303 to Bornstein describes a lyophilized synthetic pulmonary surfactant obtained by lyophilizing aqueous suspension of a combination of phospholipids, palmitic acid and a peptide.

U.S. Pat. No. 7,582,312 to Johnson describes a process of making a lyophilized synthetic pulmonary surfactant by lyophilizing a liquid formulation of phospholipids, palmitic acid and a peptide in a solvent system containing 20% or more of organic solvent.

Using the lyophilization processes described in the patents above for lyophilization of a liquid synthetic pulmonary surfactant having organic solvent in a range from 5% and above to less than 20% yielded fragile and collapsed material unacceptable for commercial distribution. Manufacturing of a synthetic pulmonary surfactant using previously described lyophilization cycles resulted in material lifting from the bottom of the vial ("levitation") which would result in reduced heat transfer, non-uniform heat distribution and yield product of varying quality attributes such as physical morphology and residual moisture.

Therefore, there is a need for improved methods of producing lung surfactant compositions and improved lung surfactant compositions. The present invention presents a solution to the problem of manufacturing a dry synthetic pulmonary surfactant, which is chemically and mechanically stable, without compromising its biological activity in the lyophilization process.

All references cited herein are incorporated herein by reference in their entireties.

BRIEF SUMMARY OF THE INVENTION

One aspect of the invention features a process of making a lyophilized synthetic pulmonary surfactant having a reduced or eliminated cake levitation during the process. The process includes providing to a lyophilizing chamber a pre-lyophilization mixture comprising at least one phospholipid and a synthetic peptide dispersed in a solvent having an organic solvent in a range of between 3% (v/v) and below 20% (v/v) of the total volume of the pre-lyophilization mixture with a remainder being water and/or buffer, wherein the pre-lyophilization mixture is filled in a container and, wherein the synthetic peptide has at least 10 amino acid residues and is represented by a formula:

$$(Z_a U_b)_c Z_d$$

wherein Z represents a hydrophilic amino acid residue and U represents a hydrophobic amino acid residue; wherein each Z is independently R, D, E or K; and each U is independently V, I, L, C, Y, or F; and wherein a is an integer with an average value of about 1 to about 5; b is an integer with an average value of about 3 to about 20; c is an integer of about 1 to about 10; and d is an integer of about 1 to about 3; lowering a temperature inside the lyophilizing chamber to begin chilling and solidifying the pre-lyophilization mixture in a freezing phase; and conducting an annealing phase prior to a primary drying phase and thereby reducing or eliminating cake levitation in the lyophilized synthetic pulmonary surfactant.

In one embodiment, the process further includes conducting the freezing phase in a process of lowering the temperature inside the lyophilizing chamber, wherein the pre-lyophilization mixture is chilled to a first temperature below −45° C. at a rate between 0.1 and 1.0° C./min and holding the pre-lyophilization mixture at the first temperature for a first period of time sufficient to solidify at least 76% of the solvent to form a first solidified mixture; conducting the annealing phase and thereby reducing or eliminating cake levitation of the first solidified mixture, wherein the first solidified mixture is (i) heated to a second temperature selected to reduce or eliminate levitation of the first solidified mixture, (ii) held at the second temperature for a second period of time sufficient to reduce or eliminate levitation of the first solidified mixture, and (iii) chilled to a third temperature below −45° C. at a rate between 0.1 to 1.0° C./min to form a second solidified mixture, wherein the second solidified mixture is held at the third temperature for a third period of time sufficient to promote separation of unfrozen organic solvent from the second solidified mixture and thereby achieve a migration of the unfrozen organic solvent to an interface between the container and the second solidified mixture; conducting a primary drying phase at a reduced pressure of 30 mT or higher, wherein the second solidified mixture is held at the fourth temperature for a fourth period of time sufficient to sublimate at least 10% of the organic solvent, followed by heating to a fourth temperature sufficient to keep the second solidified mixture from levitating in the container and retaining a structure established during the annealing phase, and further held at the fourth temperature for a fifth period of time sufficient to sublimate at least 85% of the solvent and thereby forming a third solidified mixture; and conducting a secondary drying phase at the reduced pressure for a sixth period of time sufficient to produce the lyophilized synthetic pulmonary surfactant having a residual solvent content of at most 2%.

In certain embodiments of the process, the ratio of the pre-lyophilization mixture's volume in the container to the container's volume is from about 28% to about 68%.

In certain embodiments, the process comprises providing the pre-lyophilization mixture wherein the organic solvent in the range from about 3% to about 15%. More particularly, the organic solvent is in the range from about 5% to about 10%. Even more particularly, the organic solvent in the range from about 7% to about 10%.

Any of the above described variations on the process can be practice by (1) conducting the freezing phase such that the pre-lyophilization mixture is chilled to the first temperature −50° C.±3° C. at the rate between 0.1 and 1.0° C./min; (2) conducting the annealing such that the first solidified mixture is (i) heated to the second temperature of −22° C.±3° C. at a rate of 0.1 to 1.0° C./min, (ii) held at the second temperature for the second period of time between 4 and 8 hours, (iii) chilled to the third temperature of −50° C.±3° C. at a rate between 0.1 to 1.0° C./min; and (iv) held at the third temperature for the third period of time for about 3 to 8 hours; (3) conducting the primary drying phase at a pressure of 40 mT±10 mT and temperature of −25° C.±3° C. ramped up from −50° C.±3° C., and further held at −25° C.±3° C. for 60 to 140 hours; and (4) conducting the secondary drying phase at a pressure of 40 mT±10 mT and temperature of 25° C.∓3° C. at 0.5° C./min ramped up from −25° C.±3° C. and held at 25° C.±3° C. for 4 to 10 hours.

In certain embodiments of the above-summarized process, the pre-lyophilization mixture comprises SEQ ID NO:1 (KL4 polypeptide), dipalmitoyl phosphatidylcholine (DPPC), palmitoyloleoyl phosphatidylglycerol (POPG) and palmitic acid and wherein the lyophilized synthetic pulmonary surfactant has a specific surface area at least 2.7 m2/g. More particularly, the specific surface area is in the range from about 3.7 m²/g to about 2.7 m²/g. In these processes, the lyophilized synthetic pulmonary surfactant has porosity above 40% by volume of a total area of the lyophilized synthetic pulmonary surfactant.

Another aspect of the invention features a lyophilized synthetic pulmonary surfactant composition that includes one or more phospholipids and a synthetic polypeptide having at least 10 amino acid residues and represented by a formula:

$$(Z_a U_b)_c Z_d$$

wherein Z represents a hydrophilic amino acid residue and U represents a hydrophobic amino acid residue; wherein each Z is independently R, D, E or K; and each U is independently V, I, L, C, Y, or F; and wherein a is an integer with an average value of about 1 to about 5; b is an integer with an average value of about 3 to about 20; c is an integer of about 1 to about 10; and d is an integer of about 1 to about 3, wherein the lyophilized synthetic pulmonary surfactant composition has a specific surface area at least 2.7 m²/g.

In certain embodiments, the lyophilized synthetic pulmonary surfactant has a specific surface area is in the range from about 3.7 m²/g to about 2.7 m²/g.

In certain embodiments, the lyophilized synthetic pulmonary surfactant has porosity above 40% by volume of a total area of the lyophilized synthetic pulmonary surfactant.

In certain embodiments, the lyophilized synthetic pulmonary surfactant includes SEQ ID NO:1 (KL4 polypeptide), dipalmitoyl phosphatidylcholine (DPPC), palmitoyloleoyl phosphatidylglycerol (POPG) and palmitic acid.

DETAILED DESCRIPTION OF PREFERRED EMBODIMENTS OF THE INVENTION

Figure 1:
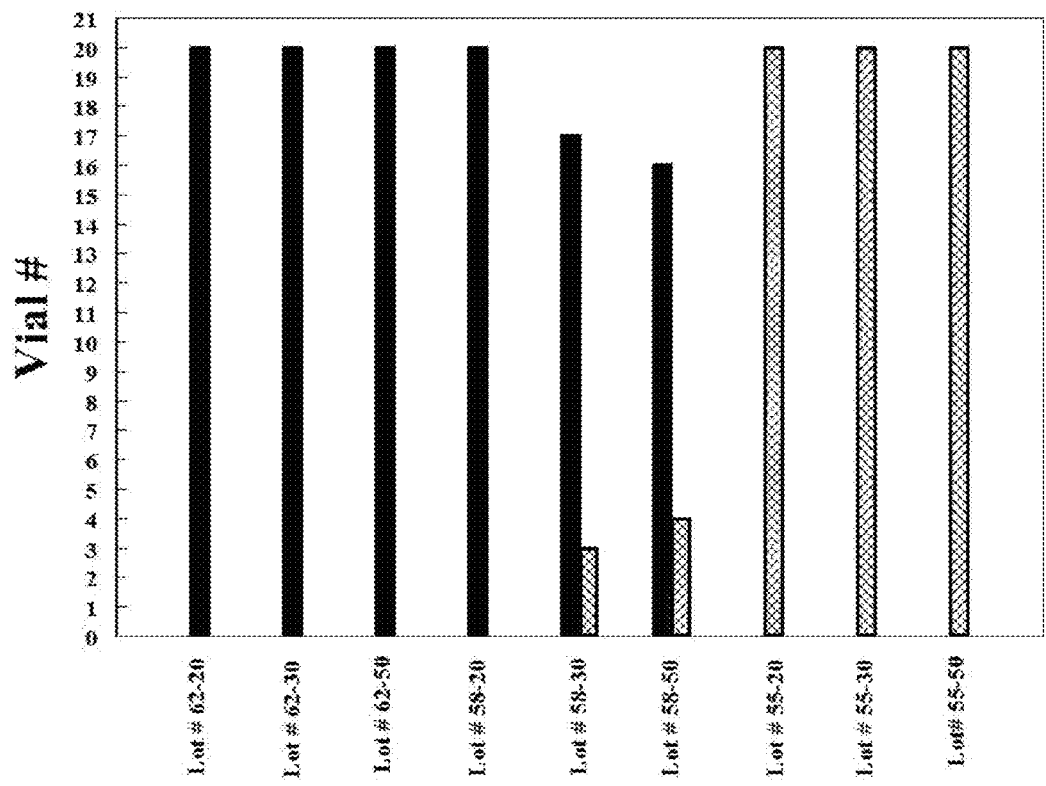
FIG. 1 is a bar graph demonstrating the movement of lyophilized material within a vial upon inversion or a lack of the movement a number of vials containing lyophilized material that moved on inversion (shown as black bars) and number of vials containing lyophilized material that did not move upon inversion (shown as shaded bars) (see Example 5).

It has been discovered that a dry synthetic pulmonary surfactant having uniformly distributed solids arranged in a mechanically stable, rigid formation capable of withstanding shipping by air and handling can be produced by an improved lyophilization cycle.

A lyophilized pharmaceutical formulation is expected to have a uniform appearance in structure and texture and good physical strength (e.g., capable to withstand shipment and handling) to be suitable for commercial distribution. The uniform appearance has been linked to improved stability and lesser variability in the drug's activity, pharmaceutical elegance of appearance, residual moisture and reconstitution time.

Lyophilizing pharmaceutical formulations containing a suspension of a liposomal composition and an organic solvent is a complicated task due to the organic solvent being trapped as a non-frozen liquid and vaporizing at a different rate as compared to other frozen liquids such as ice, and therefore, creating variance in solvent composition leading to loss of process control, difficulty maintaining the critical process parameter of chamber pressure, as well as difficulty in controlling the presence of residual solvents in the dried product.

Attempts to produce a dry synthetic pulmonary surfactant from a pre-lyophilization mixture containing organic solvent within the range from 3% to 20% using lyophilization cycles described in U.S. Pat. Nos. 5,952,303 and 7,582,312 failed to provide commercially acceptable products. The resulting products had the solids non-uniformly distributed along the surface of lyophilization vials; the solids appeared to have been levitated in the vials during the process and had a collapsed powdery surface.

Routine modifications of shelf temperatures, pressures and times did not yield the desired product having a uniform appearance in structure and texture and good physical strength (e.g., a lyophilized product capable of retaining its shape and remaining in place upon inversion of a vial it was lyophilized in). The initial step in developing the lyophilization process of the invention was to identify thermoanalytical data related to the material inherent to the specific constituents and ratios of those constituents contained within the formulation (mostly amorphous excipients also containing salts in the buffer and organic solvent). This thermal analysis was conducted by performing Freeze Drying Microscopy (FDM), Electrical Resistance (ER) and Low Temperature Differential Scanning calorimetry (LT-DSC) measurements. Thermal analysis provided critical information such as an adequate solidification temperature and threshold temperature data in which to safely dry the material while in the presence of ice during primary drying to assure retention of structure established during the freezing step. Based on knowledge of the organic constituent's character and behavior during processing, it was expected that complete solidification could not be achieved at the conditions utilized for a conventional lyophilization process. This fact presented a further significant processing challenge since the bulk solution (i.e., a pre-lyophilization mixture) comprised of a solvent system having volatile constituents, such as the organic solvent in the range from 3% to below 20%, preferably from 3% to 15%, more preferably from 5% to 10% and more preferably from 7% to 10% (v/v) of the total volume of the pre-lyophilization mixture with a remainder being water and/or buffer. Volatile constituents have melting points below temperatures achievable by the condenser. Consequently, the organic solvent could not be solidified by the condenser and are often inefficiently collected by the condenser throughout the drying process, as is the convention approach. In this process, during the drying phase of lyophilization, the organic vapors removed from the material with reduced chamber pressures, are momentarily collected on the surface of the condenser as a result of the temperature differential between the solvents in the product and the condenser. These vapors, while on the surface of the condenser, are present in a liquid state. The vapor pressure associated with each organic solvent collected as a liquid when reduced to the temperature of the condenser, is sufficiently higher than the chamber pressure, causing a subsequent conversion of the organic liquids back to the vapor state. This series of events is termed a reflux (vapor>liquid>vapor) and is continuously repeated throughout the process until, over time, the organic vapors escape the draw of the condenser and are removed from the chamber by the vacuum pump. Meanwhile, the material in a state of reflux is constantly releasing heat energy (vapor to liquid) and consuming heat energy (liquid to vapor) in order to shift from one phase to the other. The material collected on the condenser, as a result, is subjected to the uptake and release of the heat associated with reflux and is no longer able to maintain steady state conditions. If the sublimation of ice were to occur at elevated levels during reflux of the organic solvents, both the constant temperature fluctuation and the amount of free surface area of the condenser, void of refluxing organic solvent, would have an impact on the condensing of water vapor to ice, a controlled chamber pressure and ultimately, on the sublimation of ice from the product. The conventional approach to freeze drying is the sublimation of ice to form water vapor and conversion of that water vapor back to ice when collected on the condenser and is considered state of the art. Based on the challenge caused by the presence of organic solvents, in combination with the observance of cake levitation during processing, a specific two-step primary drying application was implemented to successfully overcome these effects. The intent of the two primary drying segments was to segregate the vaporization of any peripheral organic solvent from the matrix/vial interface from the sublimation of the frozen water. A mass spectrometer was utilized to measure the residual gas levels in the lyophilization chamber. These data indicated that organic solvent was being removed during this initial segment of primary drying and that the target cycle parameters for this particular segment resulted in decreased levels of organic solvent, suggesting that the process could be advanced to the second portion of primary drying. The use of this technique, by implementing a segment dedicated to removing free solvents via vaporization, resulted in the elimination of cake levitation in the target presentation for the first time. It was then reasoned that the removal of the unfrozen organic solvents in this initial segment could reduce the phenomenon of cake levitation if the affiliated segment parameters such as freezing, annealing and warming rate to primary drying could be further controlled to circumvent product mobility associated with levitation in the vial.

The inventors determined that one of the causes for levitation was inadequate solidification achieved by previously employed freezing temperatures −30° C. and −40° C. Various attempts to reduce levitation by lowering the shelf temperature to −45° C. and raising the chamber pressure during the primary drying step did not yield significant improvement. The presence of alcohol in the lyophilization mixture created a "lubricating" effect; when the cake was brought to warmer temperatures, the presence of alcohol along the sides of the vial enabled the cake to levitate. By lowering the freezing temperature to that below −45° C. and above −65° C., annealing and then conducting the primary drying at a more conservative rate, levitation was eliminated. The preferred parameters for the first freezing step were as follows: gradual cooling to a shelf temperature below −45° C. and above −65° C., preferably, −50° C. ("the first temperature"), followed by holding at the shelf temperature for a period of time sufficient to solidify at least 76% of the solvent, approximately 3-5 hours, preferably, 4 hours, all conducted at atmospheric pressure. The gradual cooling began after the pre-lyophilization mixture was equilibrated at 2-8° C. for several hours on the shelf, and then began lowering the temperature at an approximate rate of 30° C./h or during 2.5 to 4 hours. Alternate freezing rates were evaluated throughout the design process although no significant product outcomes were observed as a result.

Further, attempting to improve processing time and still maintain the required uniformity and appearance, the inventors analyzed a ratio between the volume of the sample and the size of the vial. Surprisingly, it was discovered that varying the size of the vials from 20 ml capacity to 50 ml capacity, while having the same initial amount of the fill (13.7 ml), did not provide correlating improvement in the appearance of the lyophilized cake from the smaller size vial to the largest size vial. While the 30 ml vial samples had a more uniformly distributed cake than the 20 ml vial samples, the 50 ml vial samples were less uniform than the 20 ml vial samples. The lack of improvement of material processed in the 50 ml capacity vial was likely correlated to the increased levels of cake levitation observed in this container which was associated with the resulting cake height, as compared to the cake height of the 20 cc and 30 cc vial. In scaling up the fill, the ratio between the fill volume (the volume of the pre-lyophilization mixture) and the vial (or other type of container used to hold the fill) volume should be observed to eliminate levitation of the fill material in the vial. The ratio of the fill volume to the vial volume should be from about 28% to about 68% and the preferred range is from about 35% to about 55%. It should be understood that the volumes of the vials used in these calculation are the "listed" volumes (i.e., volumes listed in catalogs and trade brochures) and not the actual internal volumes, wherein the listed volumes can differ from the actual volumes by about 10%.

Operating on the hypothesis that adding an annealing phase after a freezing step in the lyophilization process will help to create a more rigid cake with an expanded scaffold which will adhere closer to the sides and the bottom of the vial, and therefore, eliminate levitation of the solids, the inventors continued with tests in 30 ml vials. As cake levitation is a rare phenomenon, it is novel to evaluate processing behavior in varying vial sizes exclusively based on generating a greater surface area for the frozen cake to adhere to rather than the conventional approach of evaluating various vial sizes based on obtaining a minimized fill height to vial ratio.

Another objective achieved by adding the annealing phase was to obtain the increase in the sublimation rate and thereby, the decrease in the total process time, without compromising the cake appearance.

The annealing phase will now be described in detail. The annealing phase included warming of the frozen cake from −50° C.+/−3° C. to a temperature selected to reduce or eliminate levitation of the mixture ("the second temperature"), approximately −22° C.+/−3° C. at a rate of 30° C./h (a heating step) and holding for a period of time selected to reduce or eliminate levitation of the mixture, approximately 4-8 hours at −22° C.+/−3° C. (a holding step), then cooling again to 50° C.+/−3° C. at a rate of 30° C./h to −30° C.+/−3° C., 15° C./h to −40° C.+/−3° C. and 6° C./h to −50° C.+/−3° C. (a freezing step) and holding for the period of time sufficient to promote separation of unfrozen organic solvent from the solidified mixture and thereby achieve a migration of the unfrozen organic solvent to an interface between the container and the solidified mixture, approximately 3-8 hours, preferably 4 hours, at −50° C.+/−3° C., wherein all four steps were conducted at the atmospheric pressure. Thus, the annealing phase is intended to occur during the freezing phase of the lyophilization process. Inventors have observed that the use of the annealing phase increased the likelihood of preventing cake levitation from the bottom of the vial during processing by creating a less dense frozen matrix. In addition, the annealing phase promoted the migration of unfrozen solvent to the vial/matrix interface and further promoted the subsequent separation of the solvent from the product during the initial conditions used for primary drying, effectively decreasing the amount of solvent and causing the solutes, i.e., APIs and buffer salts, to be more rigid while any unfrozen water was converted to ice.

Having a better understanding of the levitation causes and intending to keep the total processing time within commercially viable time, e.g., 48 hours to 168 hours, inventors conducted further steps for sublimation of liquid phase at much lower temperatures than those described in the above mentioned patents. The primary drying phase was conducted under vacuum and included optional holding at the temperature of the previous step for a period of time sufficient to sublimate at least 10% of the organic solvent, approximately 1 hour, graduate ramping up from −50° C.+/−3° C. to −25° C.+/−3° C. at a rate of 0.1° C./min and a pressure of 40 mT+/−10 mT (a heating step), followed by a holding step at −25° C.+/−3° C. for a period of time sufficient to sublimate at least 85% of the organic solvent, approximately 60 to 140 hours, preferably for 100 hours. Selection of the temperature for the primary drying about −25° C. was based on the desire to keep the material in the vial from levitating and drying with retention of structure established during freezing. The ability to optimize the duration of the primary drying phase was enhanced by the design of the annealing phase. During the subsequent study, the intent was to further increase rates of sublimation by evaluating more dilute pre-lyophilization suspensions. The concept for this modification was based on the principle that a more dilute suspension may undergo sublimation more quickly as a result of a lower inhibition to mass transfer. Whereas, the increased volume of water would potentially lead to larger diameter ice crystal channels resulting in increased sublimation rates during primary drying. Although each solution (standard and two dilute formulations) exhibited no levitation, the drying times for both diluted formulations resulted in significantly longer process times.

A secondary drying phase was conducted by heating from the shelf temperature at the previous step, −25° C.+/−3° C. to 25° C.+/−3° C. at a rate of 30° C./hr at a pressure of 40 mT+/−10 mT (a heating step), followed by a holding step at 25° C.+/−3° C. for 4 to 10 hours, preferably for 6 hours. The resulting residual moisture at the completion of secondary drying was within specification and expectation for each study so no further design modifications were necessary. The lyophilized synthetic pulmonary surfactant obtained after the secondary drying phase had a residual solvent content of 2% or below.

The lyophilized material was then flushed with an inert gas, for example, nitrogen at 0.5 bar prior to finally fully inserting a stopper and sealing for storage.

To determine the reproducibility of the target cycle parameters, key product attributes such as temperature profiles, sublimation break temperatures and finished product characteristics were compared after processing with identical lyophilization cycles. The sublimation "break" temperature is the temperature immediately prior to the point when the product temperature sharply approaches the shelf temperature during primary drying. A product temperature "break" indicates the completion of sublimation in a given container considering the placement of the measuring thermocouple is positioned in place (bottom center) where ice is likely last to be found. For each significant step in the process (e.g., Annealing, Freezing, Primary Drying, Sublimation Break and Secondary Drying), product temperature ranges from both studies were within 0.5° C. for Annealing and Freezing, were within 1° C. for Primary Drying and the Sublimation Break, and within 1.5° C. for Secondary Drying. Based on this nominal variation, thermal behavior during processing was considered reproducible. Evaluation of the sublimation end time ranges indicated that sublimation had been completed within a range of 6 hours from study to study, also suggesting adequate reproducibility. Finally, finished product evaluation such as physical appearance, residual moisture, reconstitution time, clarity of solution, reconstituted pH, thermogravimetric mass loss (TGA) and High Temperature Differential Scanning calorimetry (HT-DSC) all yielded comparable results, further supporting the viability for reproducing consistent product quality from study to study at larger scale. The conclusion drawn from evaluation of these studies was that the lyophilization cycle parameters implemented to lyophilize synthetic pulmonary surfactant containing between 3 and below 20% organic solvent, preferably from 3% to 15%, more preferably from 5% to 10% and yet more preferably from 7% to 10% (v/v) of the total volume of the pre-lyophilization mixture, are robust and adequate to obtain consistent material with acceptable product quality attributes without the phenomenon of cake levitation.

Lyophilization was performed in a four shelf freeze dryer unit providing eight square feet of shelf space, with a 15 kilogram internal ice condenser capacity. The unit is constructed of type 304L stainless steel, certified as a pressure vessel for operating up to 20 psig for steam sterilization. Typical freeze drying equipment consists of a pressure rated chamber, a condenser, vacuum system with pressure control feature, and a circulating heat transfer fluid loop capable of a temperature range of approximately −55° C. to 50° C.

The lyophilized material appeared white, uniformly dispersed in the vials, cylindrical in shape (i.e., mimicking the shape of the vials), dense appearing, having minimal shrinkage as compared to the initial fill, having rigid structure such that it did not move on the inversion of the vial, and without traces of material or a rim above the top surface of the material. The material possessed a matte surface along the top, sides and bottom of the cake. The lyophilized material met the specification for residual moisture, DSC, reconstitution, pH, and viscosity.

The pre-lyophilization mixture and its preparation will now be described in detail. The primary components—active pharmaceutical ingredients (APIs) were pholspholipids (e.g., dipalmitoyl phosphatidylcholine (DPPC) and palmitoyloleoyl phosphatidylglycerol (POPG)), palmitic acid (PA) and a synthetic pulmonary peptide (preferably, KL4).

In certain embodiments, lung surfactant polypeptide mimics refer to polypeptides with an amino acid residue sequence that has a composite hydrophobicity of less than zero, preferably less than or equal to −1, more preferably less than or equal to −2. The composite hydrophobicity value for a peptide is determined by assigning each amino acid residue in a peptide its corresponding hydrophilicity value as described in Hopp et al., Proc. Natl. Acad. Sci. 78: 3824-3829, 1981, which disclosure is incorporated by reference. For a given peptide, the hydrophobicity values are summed, the sum representing the composite hydrophobicity value.

In certain embodiments, the amino acid sequence of the lung surfactant polypeptide mimic mimics the pattern of hydrophobic and hydrophilic residues of SP18 and perform the function of the hydrophobic region of SP18 as described in U.S. Pat. No. 5,789,381 incorporated herein in its entirety. In certain embodiments, SP-B mimics for use herein includes a polypeptide having alternating hydrophobic and hydrophilic amino acid residue regions and is characterized as having at least 10 amino acid residues represented by the formula:

$$(Z_a U_b)_c Z_d$$

Z and U are amino acid residues such that at each occurrence Z and U are independently selected. Z is a hydrophilic amino acid residue, preferably selected from the group consisting of R, D, E and K. U is a hydrophobic amino acid residue, preferably selected from the group consisting of V, I, L, C, Y, and F. The letters, "a," "b," "c" and "d" are numbers which indicate the number of hydrophilic or hydrophobic residues. The letter "a" has an average value of about 1 to about 5, preferably about 1 to about 3. The letter "b" has an average value of about 3 to about 20, preferably about 3 to about 12, most preferably, about 3 to about 10. The letter "c" is 1 to 10, preferably, 2 to 10, most preferably 3 to 6. The letter "d" is 1 to 3, preferably 1 to 2.

By stating that the amino acid residue represented by Z and U is independently selected, it is meant that each occurrence, a residue from the specified group is selected. That is, when "a" is 2, for example, each of the hydrophilic residues represented by Z will be independently selected and thus can include RR, RD, RE, RK, DR, DD, DE, DK, etc. By stating that "a" and "b" have average values, it is meant that although the number of residues within the repeating sequence (ZaUb) can vary somewhat within the peptide sequence, the average values of "a" and "b" would be about 1 to about 5 and about 3 to about 20, respectively.

In certain embodiments, exemplary SP-B polypeptide mimics that can be used in the present invention include, but are not limited to, those shown in the Table of Pulmonary Surfactant Mimetic Peptides.

Table of Pulmonary Surfactant Mimetic Peptides

| Designation[1] | SEQ ID NO | Amino Acid Residue Sequence |
|---|---|---|
| KL4 | 1 | KLLLLKLLLLKLLLLKLLLLK |
| DL4 | 2 | DLLLLDLLLLDLLLLDLLLLD |

-continued

Table of Pulmonary Surfactant Mimetic Peptides

| Designation[1] | SEQ ID NO | Amino Acid Residue Sequence |
|---|---|---|
| RL4 | 3 | RLLLLRLLLLRLLLLRLLLLR |
| RL8 | 4 | RLLLLLLLLRLLLLLLLLRLL |
| R2L7 | 5 | RRLLLLLLLRRLLLLLLLRRL |
|  | 6 | RLLLLCLLLRLLLLCLLLR |
|  | 7 | LLLLLCLLLRLLLLCLLLRLL |
|  | 8 | RLLLLCLLLRLLLLCLLLRLLLLCLLLR DLLLDLLLDLLLDLLLDLLLD |
| RCL1 | 9 | RLLLLCLLLRLLLLCLLLR |
| RCL2 | 10 | RLLLLCLLLRLLLLCLLLRLL |
| RCL3 | 11 | RLLLLCLLLRLLLLCLLLRLLLLCLLLR |
| KL8 | 12 | KLLLLLLLLKLLLLLLLLKLL |
| KL7 | 13 | KKLLLLLLLKKLLLLLLLKKL |

[1]The designation is an abbreviation for the indicated amino acid residue sequence.

Examples of phospholipids useful in the compositions delivered by the invention include native and/or synthetic phospholipids. Phospholipids that can be used include, but are not limited to, phosphatidylcholines, phospatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidyl serine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, and egg phosphatidylcholine (EPC).

Examples of fatty acids and fatty alcohols useful in these mixtures include, but are not limited to, sterols, palmitic acid, cetyl alcohol, lauric acid, myristic acid, stearic acid, phytanic acid, dipamlitic acid, and the like. Preferably; the fatty acid is palmitic acid and preferably the fatty alcohol is cetyl alcohol.

Examples of fatty acid esters useful in these mixtures include, but are not limited to, methyl palmitate, ethyl palmitate, isopropyl palmitate, cholesteryl palmitate, palmityl palmitate sodium palmitate, potassium palmitate, tripalmitin, and the like.

An example of a semi-synthetic or modified natural lipid is any one of the lipids described above which has been chemically modified. The chemical modification can include a number of modifications; however, a preferred modification is the conjugation of one or more polyethylene glycol (PEG) groups to desired portions of the lipid. Polyethylene glycol (PEG) has been widely used in biomaterials, biotechnology and medicine primarily because PEG is a biocompatible, nontoxic, nonimmunogenic and water-soluble polymer. In the area of drug delivery, PEG derivatives have been widely used in covalent attachment (i.e., "PEGylation") to proteins to reduce immunogenicity, proteolysis and kidney clearance and to enhance solubility.

Lipids that have been conjugated, with PEG are referred to herein as "PEG-lipids." Preferably, when PEG-lipids are used in methods and compositions of this invention, they are present in alcohols and/or aldehydes.

Other excipients can be combined with the lung surfactant polypeptide, one or more lipids, and organic solvent system before lyophilization including, but not limited to, various sugars such as dextrose, fructose, lactose, maltose, mannitol, sucrose, sorbitol, trehalose, and the like, surfactants such as, for example, polysorbate-80, polysorbate-20, sorbitan trioleate, tyloxapol and the like, polymers such as PEG, dextran and the like, salts such as NaCl, $CaCl_2$ and the like, alcohols, such as cetyl alcohol, and buffers.

Preferably, the pulmonary surfactant peptide is combined with phospholipids and free fatty acids or fatty alcohols, e.g., DPPC (dipalmitoyl phosphatidylcholine), POPG (palmitoyl-oleyl phosphatidylglycerol) and palmitic acid (PA). See, for example, U.S. Pat. No. 5,789,381 the disclosure of which is incorporated herein by reference in its entirety and for all purposes.

The first step in preparing a pre-lyophilized mixture is to obtain a substantially homogenous liquid mixture of the pulmonary surfactant peptide, one or more lipids, in an organic solvent system containing 93-100% organic solvent, preferably 95% ethanol. By the term "substantially homogeneous" it is meant that the components are uniformly dispersed in each other, for example, as in a solution. The APIs are mixed in the organic solvent system heated to 45° C.±5° C. until a solution is obtained. The resulting solution is then filtered through a sterile filter (0.22 micron) into a buffer, preferably, tris(hydroxymethyl)aminomethane (TRIS) buffer solution heated to 45° C.±5° C. and stirred to produce the pre-lyophilization mixture in a form of a liposomal suspension, having the concentration of the organic solvent in a range of between 3% and below 20% (v/v) of the total volume of the pre-lyophilization mixture, preferably from 3% to 15%, more preferably from 5% to 10% and yet more preferably from 7% to 10% with a remainder being water and/or buffer.

In certain preferred embodiments, a mixture of pulmonary surfactant peptide, phospholipids and free fatty acids or fatty alcohols, for example, DPPC (dipalmitoyl phosphatidylcholine) and POPG (palmitoyl-oleyl phosphatidylglycerol) and palmitic acid (PA) is combined with the organic solvent system to form the substantially homogenous liquid mixture. The individual components can be present in the mixture in any concentration. The total concentration of phospholipid in the dispersion can range, for example, from about 1 to over about 80 mg-total phospholipid content/ml. Suitable buffers include, but are not limited to, tris acetate, tris hydrochloride, sodium phosphate, potassium phosphate, and the like. The buffers are typically commercially available.

In a preferred embodiment, the liposomal suspension for use in the methods of the present invention comprises DPPC, POPG, PA and KL4 (weight ratio of approximately 7.5:2.5:1.35:0.267) in a physiologically acceptable solvent having the concentration of the organic solvent in a range of between 3% and below 20% (v/v) of the total volume of the pre-lyophilization mixture, preferably from 3% to 15%, more preferably from 5% to 10% and yet more preferably from 7% to 10% with a remainder being water and/or buffer.

In certain embodiments, the organic solvent system further comprises additional excipients, including, but not limited to, various sugars such as dextrose, fructose, lactose, maltose, mannitol, sucrose, sorbitol, trehalose, and the like, surfactants such as, for example, polysorbate-80, polysorbate-20, sorbitan trioleate, tyloxapol and the like, polymers such as PEG, dextran and the like, salts such as NaCl, $CaCl_2$, and buffers. In certain preferred embodiments, the organic solvent system is substantially free of salt. In certain preferred embodiments, the organic solvent system is substantially free of NaCl.

In certain embodiments, the organic solvent system can be prepared by combining all of the system components. For example, in certain embodiments wherein the organic solvent consists of organic solvent and an aqueous medium at room temperature, the aqueous medium and organic solvent can be combined to make up the organic solvent system. Preferably, the organic solvent system is an emulsion or a miscible solution.

The organic solvent selected is preferably compatible with sterile filtration and lyophilization. Preferably, organic solvents of this invention are selected from the group consisting of lower oxy hydro carbons, lower halohydrocarbons, lower haloxyhydrocarbons, lower sulfoxyhydrocarbons, lower cyclohydrocarbons and combinations thereof.

Suitable organic solvents for use in this invention, include, but are not limited to, isopropyl alcohol, methanol, ethanol, acetone, acetonitrile, cyclohexane, chlorobutanol, dimethylsulfoxide, t-butanol, hexanol, benzyl alcohol, acetic acid, pentanol (1-pentanol), n-butanol, n-propanol, methyl acetate, dimethyl carbonate, methyl ethyl ketone, methyl isobutyl ketone, carbon tetrachloride, hexafluoroacetone, chlorobutanol, dimethyl sulfone, cyclohexane, and combinations thereof. Preferable solvents include lower alkanols, such as t-butanol, ethanol, isopropyl alcohol, and the like. A particularly preferred solvent of the invention is ethanol.

In certain preferred embodiments, the lung surfactant composition is lucinactant or another pulmonary surfactant formulation comprising the synthetic surfactant peptide KLLLLKLLLLKLLLLKLLLLK (KL4; SEQ ID NO:1). In certain preferred embodiments, the lyophilized pulmonary surfactant of the invention when reconstituted would yield a combination of APIs: DPPC, POPG, PA and the KL4 peptide in a weight ratio of approximately 7.5:2.5:1.35:0.267) or in the same weight ratio as in SURFAXIN® (lucinactant) liquid synthetic pulmonary surfactant by Discovery Laboratories, Inc. (Warrington, Pa., USA). In certain embodiments, the pulmonary surfactant composition is formulated at concentrations of, for example, 10, 20, and 30 mg/ml of phospholipid content. In certain other embodiments, the pulmonary surfactant composition is formulated at greater concentrations, e.g., 60, 90, 120 or more mg/ml phospholipid content, with concomitant increases in KL4 concentration.

In certain exemplary embodiments of the present invention, the relative amounts of pulmonary surfactant peptide, phospholipids and free fatty acids or fatty alcohols is about 1 part by weight of a synthetic surfactant peptide; about 20 to about 150 parts by weight of a phospholipid per part weight of the synthetic surfactant peptide; about 0 to about 25 parts by weight of a free fatty acid or fatty alcohol per part weight of the synthetic surfactant peptide. In certain embodiments the relative amount of organic solvent system is in the range of more than 62.5 and less than 250 parts by weight per part weight of the lung surfactant peptide. In certain embodiments, the organic solvent system is present in a range from 80 to 125 parts by weight per part weight of the lung surfactant peptide. In certain exemplary embodiments, the relative amounts of lung surfactant peptide, phospholipids and free fatty acids or fatty alcohols is about 1 part by weight of a lung surfactant peptide, such as, for example, KL4; about 20 about 100 parts by weight of DPPC; 0 to about 50 parts by weight of POPG; and about 0 to about 25 parts by weight of palmitic acid.

The lyophilized material of the invention appeared white, uniformly dispersed in the vials, cylindrical in shape (i.e., mimicking the shape of the vials), dense, having minimal shrinkage as compared to the initial fill, having rigid structure such that it did not move on the inversion of the vial, and without traces of material or a rim above the top surface of the material. The lyophilized synthetic pulmonary surfactant of the invention prepared by the above described method has larger specific surface area (at least at least 2.7 $m^2/g$) and larger total pore area (at least 40%) than that of pulmonary surfactants prepared by other lyophilization methods.

The lyophilized material passed the inspection for residual moisture, reconstitution time, pH, viscosity, and its biological activity. The lyophilized material was reconstituted with 10 ml of sterile water for injection (WFI) and the solids were dispersed within 20 to 30 seconds. The pH was in the range of 7.6-7.9. Viscosity measured by using Brookfield Viscometer, Model LVDV-II at 37° C. (Brookfield Engineering Laboratories, Inc., Middleboro, Mass.) was in the range of 77-105 cP (0.077-0.105 Pa s). Samples were analyzed by Pulsating Bubble Surfactormeter (PBS) Model EC-PBS-B (Electronetics Corporation, USA, now General Transco Inc., Largo, Fla.) at 37° C. for the ability to lower surface tension (e.g., biological activity); the average surface tension measurements were between 2 and 7 dynes/cm ($2 \times 10^{-3}$ to $7 \times 10^{-3}$ N/m). The acceptable value for an effective pulmonary surfactant is below 10 dynes/cm (0.01N/m).

One way to characterize a lyophilized material is to measure its specific surface area. Specific surface area is a measure of the exposed surface of a solid sample on the molecular scale. The BET (Brunauer Emmet and Teller) surface area analysis method is an established model used to determine the specific surface area of solids by physical adsorption of gas molecules (see U.S. Pharmacopeia Title: <846> Specific Surface Area (http://www.pharmacopeia.cn/v29240/usp29nf24s0_c846.html)). Samples are commonly prepared by heating while simultaneously evacuating or flowing gas over the sample to remove the liberated impurities. The prepared samples are then cooled with liquid nitrogen or krypton and analyzed by measuring the volume of gas adsorbed at specific pressures. The BET 11-point tests were conducted on selected samples by Micromeritics Pharmaceutical Services (Norcross, Ga.) using ASAP® 2420 Accelerated Surface Area and Porosimetry System (Micromeritics Instruments Co., Norcross, Ga.). Samples were outgassed at 25° C. for 16 hours under vacuum. 100% krypton was used as adsorbate. Analysis Bath Temperature was about 77K. The following parameters were measured: Sample Mass (g), Cold Free Space ($cm^3$), Warm Free Space ($cm^3$), Saturation Pressure (Po) (mm Hg), Absolute Pressure (P) (mm Hg), and Elapsed Time. Isotherm Linear Plots were calculated for each sample, wherein the Y axis was Quantity Adsorbed (cm³/g STP) and the X axis was Relative Pressure (P/Po). STP is known as standard temperature and pressure, i.e., temperature of 273.15 K and atmospheric pressure (1.013×10⁵ Pa). Data are presented in Examples below.

Another parameter useful in characterization of morphology of lyophilized material is its porosity defined as a ratio of the volume of all the pores in a material to the volume of the whole. The porosity of the lyophilized material was determined using a scanning electron microscope (SEM) JEOL 6480 Scanning Electron Microscope (JEOL, Japan). The samples were removed from the vials by cutting the vial top with a diamond saw and cut in half across their width. The cross sections of the cut samples were placed in the SEM unit and visualized at magnification (×) of 20 and 100. The analysis was run under vacuum at room temperature. Surface area of magnification ×20 was approximately 6.4 mm×5.1 mm. Surface area of magnification ×100 was approximately 1,200 microns×965 microns.

Figure 3A:
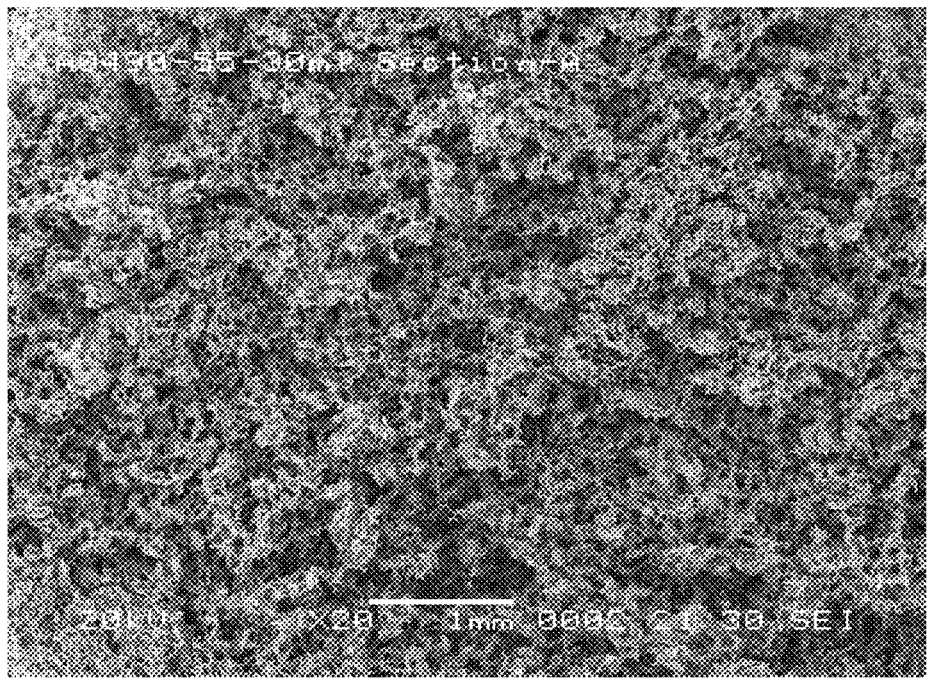
FIGS. 3A and 3B are scanning electron microscope (SEM) images of the lyophilized pulmonary surfactant of the invention made in 30 ml vials, at a magnification of ×20, surface A and surface B, respectively.
Figure 3B:
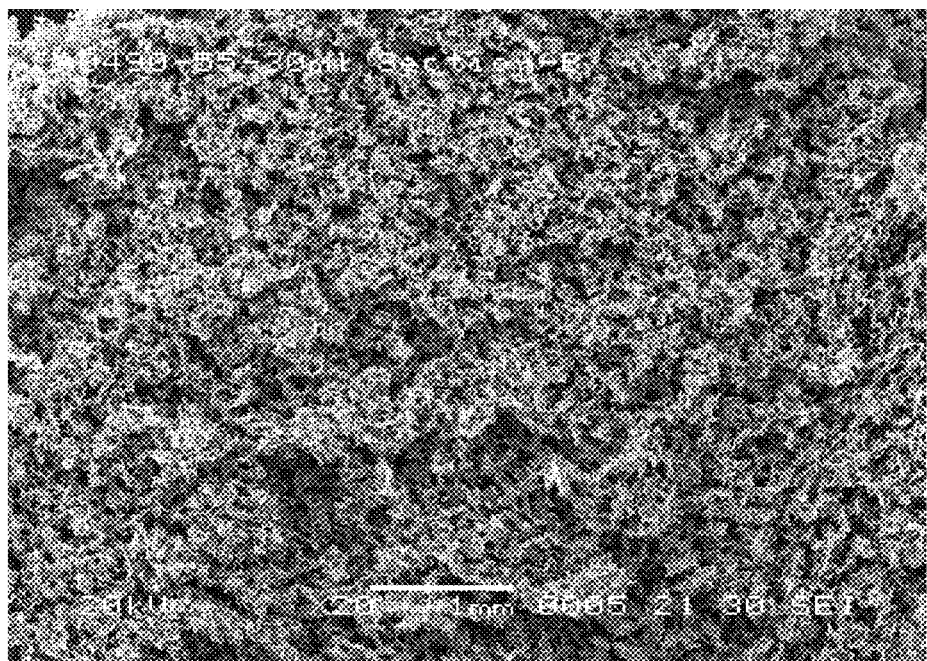
Figure 4A:
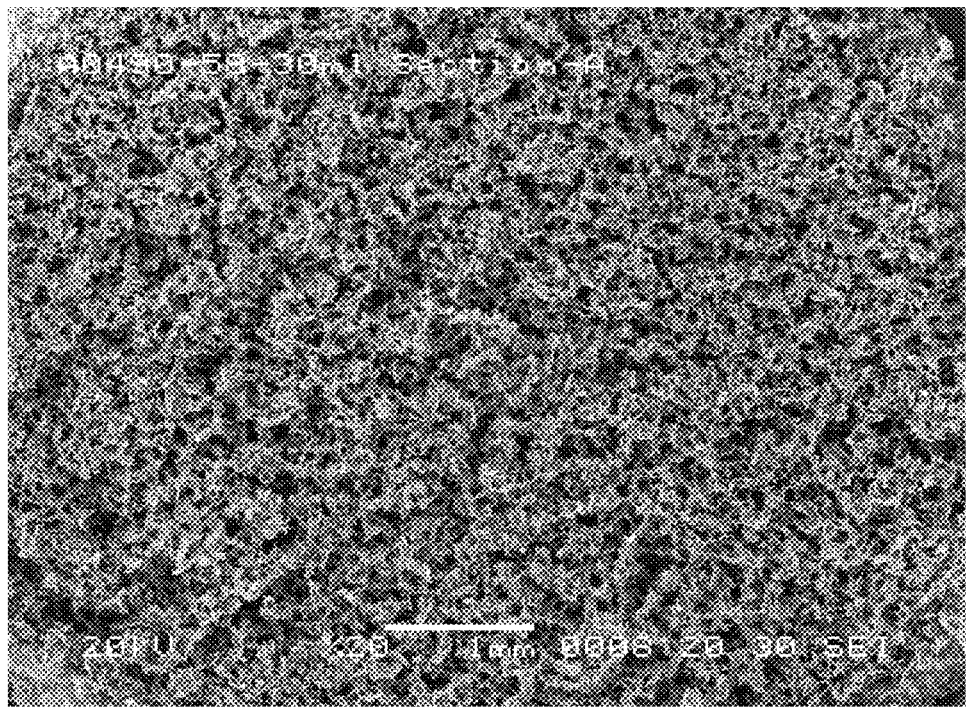
FIGS. 4A and 4B are SEM images of the lyophilized pulmonary surfactant Formulation II made by the Bornstein Lyo Cycle in 30 ml vials as described in Example 3, at a magnification of ×20, surface A and surface B, respectively.
Figure 4B:
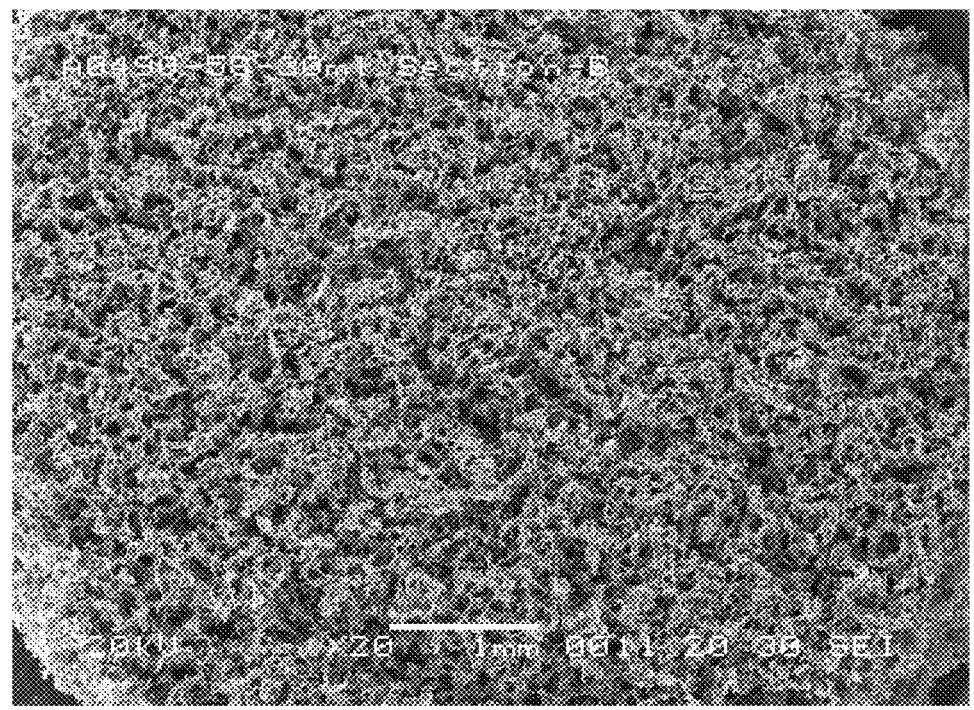
Figure 5A:
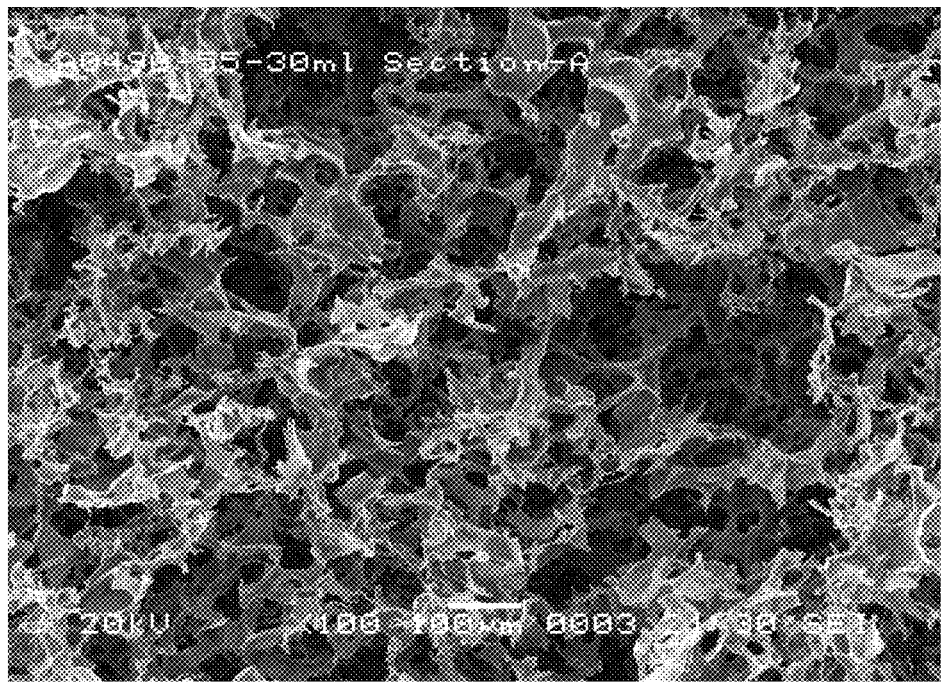
FIGS. 5A and 5B are SEM images of the lyophilized pulmonary surfactant of the invention made in 30 ml vials, at a magnification of ×100, surface A and surface B, respectively.
Figure 5B:
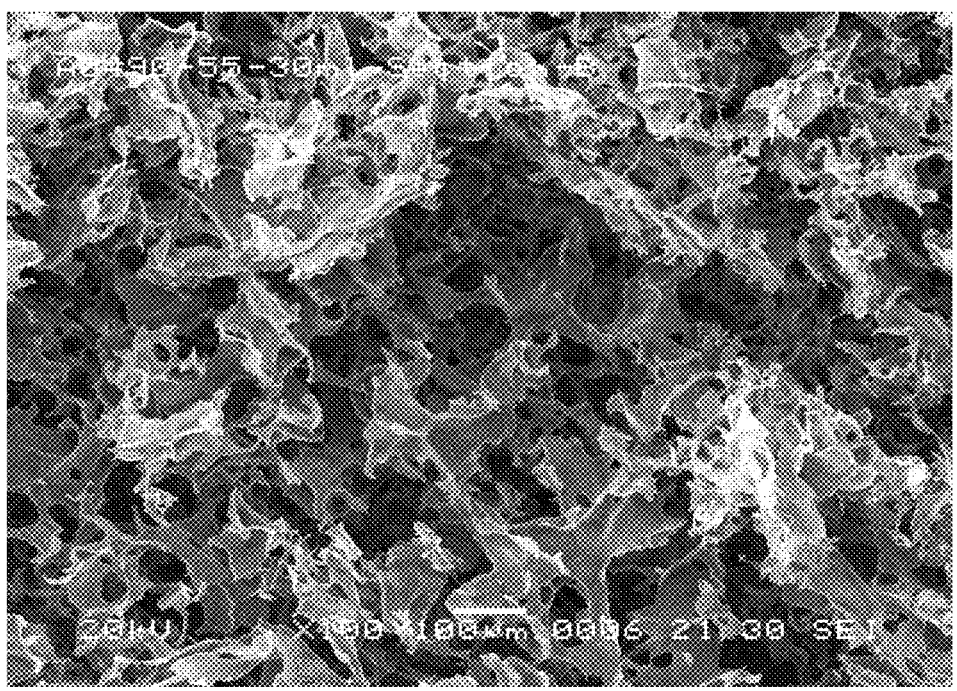
Figure 6A:
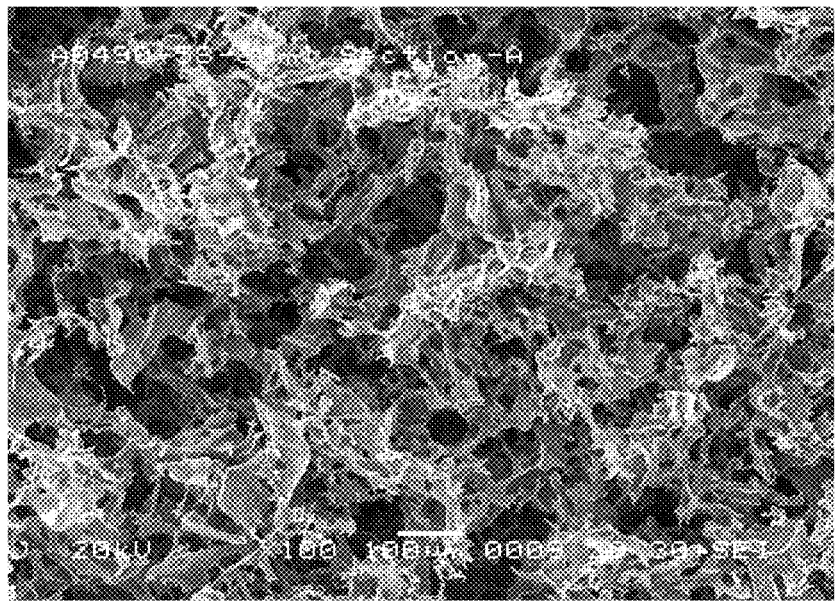
FIGS. 6A and 6B are SEM images of the lyophilized pulmonary surfactant Formulation II made by the Bornstein Lyo Cycle in 30 ml vials as described in Example 3, at a magnification of ×100, surface A and surface B, respectively.
Figure 6B:
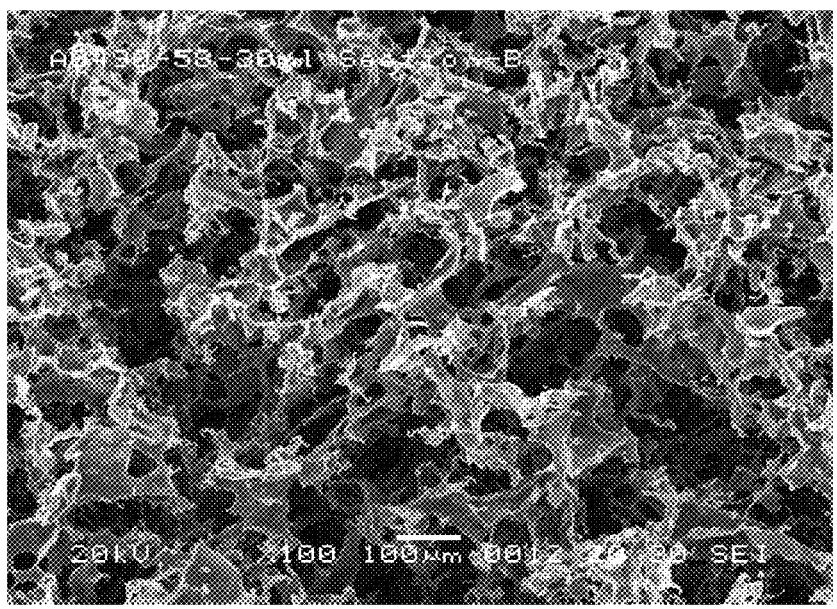

The SEM micrographs of cross sectioned scaffolds reveal microchannel or porous structure over the entire cross section of each sample. Two vintage points were selected for imaging: the top of the cake (uncut area) as "surface A" and the interior of the cake as "surface B". FIGS. 3A and 3B show the magnified image of the lyophilized pulmonary surfactant of the invention made in 30 ml vials, at a magnification of ×20, surface A and surface B, respectively. FIGS. 4A and 4B show the magnified image of the lyophilized pulmonary surfactant Formulation II made by the Bornstein Lyo Cycle in 30 ml vials as described in Example 3, at a magnification of ×20, surface A and surface B, respectively. FIGS. 5A and 5B show the magnified image of the lyophilized pulmonary surfactant of the invention made in 30 ml vials, at a magnification of ×100, surface A and surface B, respectively. FIGS. 6A and 6B show the magnified image of the lyophilized pulmonary surfactant Formulation II made by the Bornstein Lyo Cycle in 30 ml vials as described in Example 3, at a magnification of ×100, surface A and surface B, respectively.

Notably, Formulation III (A0490-62) made as described in Example 4 using the "Johnson Lyo Cycle" could not be analyzed with the SEM due to its fragility. The cake did not tolerate even a slight pressure of the saw and fell apart. Comparing the total pore area of Formulation I (A0490-55) made as described in Example 2 using the Novel Lyo Cycle with the total pore area of Formulation II (A0490-58) made as described in Example 3 using the "Bornstein Lyo Cycle", it was observed that Formulation I was more porous with the absolute difference of at least 11%.

MOTIC® Images Plus 2.0 software (Motic Group Co., Ltd, Xiamen, China) for a microscope was used to calculate the open area in the selected image. The relief filter was applied to highlight the open areas and then using the auto segment and auto calculation features the open surface area were calculated. This approach minimized manual manipulation of the data and removed bias between comparing images. For Formulation I, the pore areas constituted 49.1% of the measured area for the top of the sample (Surface A) and 50.5% of the measured area for the interior of the cake (Surface B). For Formulation II, the pore areas constituted 37.3% of the measured area for the top of the sample (Surface A) and 36.7% of the measured area for the interior of the cake (Surface B). The respective differences were 11.8% and 13.8%.

The manual pore calculation was conducted to test the accuracy of the above approach for samples shown in FIG. 5A (Formulation I, surface A, ×100) and FIG. 6A (Formulation II, surface A, ×100). Each micrograph was trimmed to the size 6.4 mm (width) and 3.9 mm (height), and 20 "pores" were measured for height and width in each picture and compared.

The lyophilized synthetic pulmonary surfactant composition of the invention has the unique combination of a larger surface area (at least 2.7 m²/g), larger porosity (above 40% by volume) and demonstrated rigidity, e.g., observed resistance to movement when inverted and also resistant to movement when a vial containing the material was tapped. A more rigid mass would correlate to reduced molecular mobility, a precursor to chemical reactions, and therefore a more stable product.

It was previously observed that out of four APIs, sinapultide or KL4 peptide degrades faster in a liquid environment than in a solid state as a lyophilized material (see U.S. Pat. No. 5,952,303 to Bornstein). Based on the belief that the uniform appearance of the lyophilized formulation is also a manifestation of a more stable product, inventors anticipate that the lyophilized formulation obtained by the inventive method described herein will demonstrate improved stability of at least KL4 peptide within at least 3 months of storage at 25° C. It is expected that within a longer storage term, e.g., 6 months and 9 months at 25° C. and also if stored at higher temperatures, e.g., 30° C. and 40° C., stability of KL4 and other APIs will be statistically better for the lyophilized formulation obtained by the inventive method as compared to the lyophilized formulation made by other lyophilization processes. The improvement in stability is expected to be at least above 2%, at least above 5% or at least above 10%.

Lyophilized pulmonary surfactants of the invention can be reconstituted with water or other pharmaceutically acceptable diluents. The use of pulmonary surfactants, liquid or lyophilized, has been previously described. The novel lyophilized pulmonary surfactants exhibits excellent cake and ability to withstand movement and shipping, which are necessary attributes of pharmaceutical product.

The invention will be illustrated in more detail with reference to the following Examples, but it should be understood that the present invention is not deemed to be limited thereto.

EXAMPLES

Example 1

Lyophilization was performed using the novel process and previously published processes described in U.S. Pat. Nos. 5,952,303 and 7,582,312 to demonstrate the differences imparted by each process on the resulting lyophilized product.

Materials: the ingredients in the formulations lyophilized by each of the three processes are summarized below in Table 1. Actual amounts are adjusted for purity of raw materials.

TABLE 1

Raw Materials for Formulations I, II, and III (3000 g Batch Size)

| Materials | Amount (mg) per gram of formulation | Amount (g) per batch |
|---|---|---|
| KL₄ (API) | 0.74 mg | 2.22 g |
| DPPC (API) | 18.00 mg | 54.00 g |
| POPG, Na (API) | 5.82 mg | 17.47 g |
| PA (API) | 3.113 mg | 9.38 g |
| 95% Ethanol | 0.105 mg | 316 g |
| TRIS Buffer: | | |
| NaCl | 5.83 mg | 17.49 g |
| Tromethamine | 1.86 mg | 5.57 g |
| Water | 0.859 g | 2578 g |

Procedure: two 3000 gram batches were prepared for each of the three processes. A syringe was used to charge to the standard fill weight of 13.7 grams per vial. Preparation of a pre-lyophilization mixture: the APIs were dissolved in 95% ethanol at 46° C.±1° C. to obtain a solution. The resultant solution was sterile filtered using pressure through a 0.22 micron 33 mm filter into stirring tris(hydroxymethyl)aminomethane (TRIS) buffer solution at 45° C.±2° C. to produce a liposomal formulation with a final ethanol concentration of 10% (w/w). After cooling to a temperature below 30° C., the resultant liposomal formulation, i.e., the pre-lyophilization mixture, was transferred into 20, 30 and 50 mL borosilicate glass lyophilization vials at a fill volume of 13.7 g/vial. The resultant lyophilized material was stored at 5° C.

Example 2

Formulation I. The pre-lyophilization mixture from Table 1 was used as a fill in 20, 30 and 50 mL glass vials and lyophilized using the novel lyophilization method described above. Table 2 summarizes parameters of the lyophilization process.

TABLE 2

Parameters for the Novel Lyophilization Process

| Phases of Lyophilized Cycle | Steps | Parameters |
|---|---|---|
| Beginning Phase* | Initial Shelf Temperature: | 5° C. hold for 2 hours |
| Freezing Phase* | Cooling Step | −20° C. at 1.0° C./min |
|  | Cooling Step | −30° C. at 0.5° C./min |
|  | Cooling Step | −40° C. at 0.25° C./min |
|  | Cooling Step | −50° C. at 0.10° C./min |
|  | Hold Step | −50° C. for 4 hours |
| Annealing Phase* | Heating Step | −22° C. at 0.5° C./min |
|  | Annealing Step | −22° C. for 4 hours |
|  | Cooling Step | −30° C. at 0.5° C./min |
|  | Cooling Step | −40° C. at 0.25° C./min |
|  | Cooling Step | −50° C. at 0.10° C./min |
|  | Hold Step | −50° C. for 4 hours |
| Primary Drying Phase** | Vacuum: | 40 mT |
|  | Hold Step | −50° C. for 1 hour |
|  | Heating Step | −25° C. at 0.10° C./min |
|  | Hold Step | −25° C. for 100 hours |
| Secondary Drying Phase** | Heating Step | 25° C. at 0.5° C./min |
|  | Hold Step | 25° C. for 6 hours |
| Finishing Phase** | Backflush: | $N_2$ to ½ bar prior to sealing vials |

*The phase is conducted at the atmospheric pressure.
**The phase is conducted under vacuum.

Example 3

Formulation II. The pre-lyophilization mixture from Table 1 was used as a fill in 20, 30 and 50 mL glass vials and lyophilized using the process described in U.S. Pat. No. 5,952,303 to Bornstein ("Bornstein Lyo Cycle"). Table 3 summarizes parameters of the process.

TABLE 3

Lyophilization Parameters for Bornstein Lyo Cycle

| | |
|---|---|
| Initial Shelf Temperature*: | 25° C. |
| Cooling Step* | −40° C. at 1.0° C./min |
| Hold Step* | −40° C. for 2 hours |
| Vacuum: | 100 mT |
| Heating Step** | 0° C. at 0.5° C./min |
| Hold Step** | 0° C. for 48 hours |
| Heating Step** | 26° C. at 0.5° C./min |
| Hold Step** | 26° C. for 12 hours |
| Backflush**: | $N_2$ to ½ bar prior to sealing vials |

*The phase is conducted at the atmospheric pressure.
**The phase is conducted under vacuum.

Example 4

Formulation III. The pre-lyophilization mixture from Table 1 was used as a fill in 20, 30 and 50 mL glass vials and lyophilized using the process described in U.S. Pat. No. 7,582,312 to Johnson ("Johnson Lyo Cycle"). Table 4 summarizes parameters of the process.

TABLE 4

Lyophilization Parameters for Johnson Lyo Cycle

| | |
|---|---|
| Initial Shelf Temperature*: | 25° C. |
| Cooling Step* | −30° C. at 1.0° C./min |
| Hold Step* | −30° C. until vials reach temperature |
| Vacuum**: | 500 mT |
| Heating Step** | 0° C. at 1° C./min |
| Hold Step** | Hold until vials reach temperature |
| Backflush**: | $N_2$ to ½ bar prior to sealing vials |

*The phase is conducted at the atmospheric pressure.
**The phase is conducted under vacuum.

Example 5

Evaluation of lyophilized material physical appearance. 20 vials were randomly selected. Lots 55-20, 55-30 and 55-50 correspond to Formulation I in 20, 30 and 50 ml vials respectively. Lots 58-20, 58-30 and 58-50 correspond to Formulation II in 20, 30 and 50 ml vials respectively. Lots 62-20, 62-30 and 62-50 correspond to Formulation III in 20, 30 and 50 ml vials respectively. All categorical variables were summarized using frequency and, where appropriate, percent. All continuous variables were summarized using mean and Standard Deviation (SD), with median and range (minimum, maximum) used for selected assessments. Formulations I, II and III lyophilized in 20, 30 and 50 ml vials were visually inspected for signs of levitation such as a white ring above the initial fill height. The liquid fill height for a 20 ml vial was 25 mm; for a 30 ml vial, the liquid fill height was 20 mm; for a 50 ml vial, the liquid fill height was 15 mm.

Figure 2:
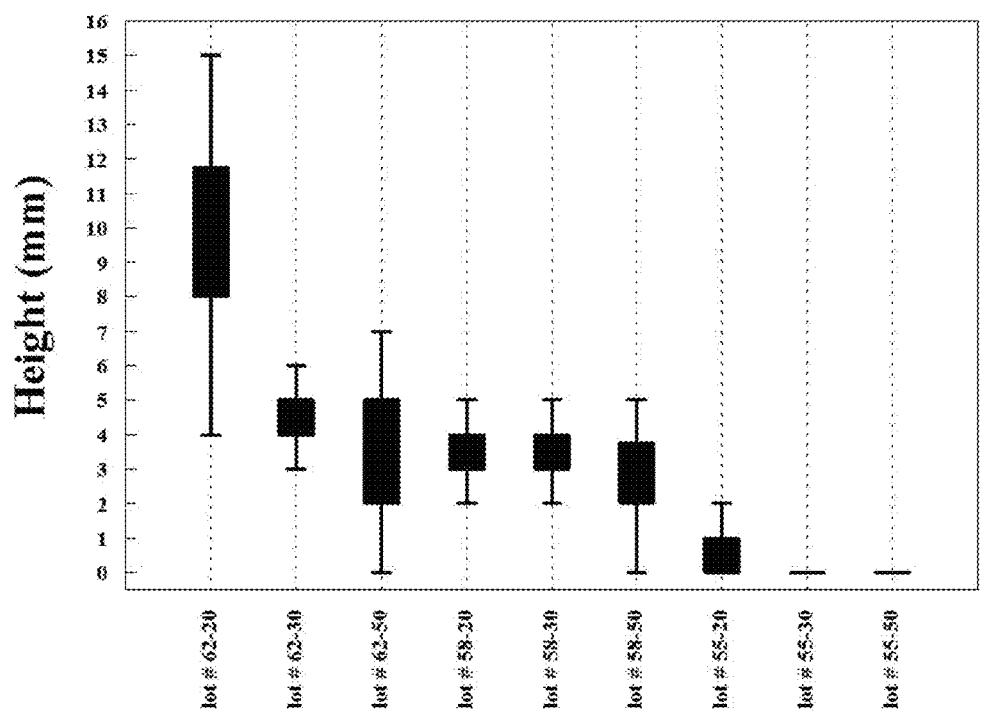
FIG. 2 is a graph demonstrating levitation of material during the lyophilization process (see Example 5).

Measurement of actual levitation distance and measurement from the bottom of the vial to the white ring above initial fill height minus the initial fill height were taken and presented in Table 5 and FIG. 2.

TABLE 5

| | Levitation Height, mm | | | | | | | | |
|---|---|---|---|---|---|---|---|---|---|
| VIAL NUMBER | lot # 62-20 | lot # 62-30 | lot # 62-50 | lot # 58-20 | lot # 58-30 | lot # 58-50 | lot # 55-20 | lot # 55-30 | lot # 55-50 |
| 1 | 11 | 4 | 0 | 3 | 4 | 4 | 1 | 0 | 0 |
| 2 | 6 | 4 | 0 | 2 | 5 | 0 | 1 | 0 | 0 |

TABLE 5-continued

Levitation Height, mm

| VIAL NUMBER | lot # 62-20 | lot # 62-30 | lot # 62-50 | lot # 58-20 | lot # 58-30 | lot # 58-50 | lot # 55-20 | lot # 55-30 | lot # 55-50 |
|---|---|---|---|---|---|---|---|---|---|
| 3 | 15 | 4 | 0 | 3 | 3 | 5 | 0 | 0 | 0 |
| 4 | 7 | 5 | 0 | 2 | 3 | 3 | 0 | 0 | 0 |
| 5 | 20 | 4 | 4 | 2 | 3 | 3 | 0 | 0 | 0 |
| 6 | 10 | 6 | 5 | 2 | 3 | 4 | 0 | 0 | 0 |
| 7 | 7 | 3 | 4 | 3 | 4 | 3 | 0 | 0 | 0 |
| 8 | 12 | 5 | 7 | 3 | 4 | 4 | 2 | 0 | 0 |
| 9 | 14 | 5 | 4 | 4 | 4 | 4 | 1 | 0 | 0 |
| 10 | 8 | 4 | 3 | 3 | 3 | 3 | 2 | 0 | 0 |
| 11 | 10 | 5 | 5 | 4 | 2 | 3 | 0 | 0 | 0 |
| 12 | 10 | 5 | 6 | 5 | 3 | 0 | 0 | 0 | 0 |
| 13 | 9 | 4 | 5 | 4 | 3 | 2 | 0 | 0 | 0 |
| 14 | 12 | 4 | 5 | 3 | 4 | 1 | 0 | 0 | 0 |
| 15 | 8 | 6 | 10 | 3 | 2 | 3 | 1 | 0 | 0 |
| 16 | 4 | 5 | 5 | 3 | 3 | 0 | 1 | 0 | 0 |
| 17 | 11 | 3 | 2 | 4 | 2 | 3 | 0 | 0 | 0 |
| 18 | 9 | 5 | 3 | 4 | 3 | 2 | 0 | 0 | 0 |
| 19 | 10 | 5 | 2 | 4 | 2 | 2 | 0 | 0 | 0 |
| 20 | 8 | 5 | 4 | 3 | 3 | 2 | 0 | 0 | 0 |

Samples of Formulation I (lots 55-30 and 55-50) (the lyophilized pulmonary surfactant of the invention) in 30 and 50 ml vials did not have any signs of levitation while samples in 20 ml vials (lot 55-20), have some slight levitation up to 2 mm in 7 out 20 samples. Formulation II samples (58-20, 58-30 and 58-50) in all three sizes and well as Formulation III samples (62-20, 62-30 and 62-50), with Formulation III samples in 20 ml vials being the worst, all display signs of levitation during the lyophilization process. Clearly, using the novel lyophilization process, the problem of levitation has been significantly reduced or eliminated.

Twenty randomly selected vials of Formulations I, II and III lyophilized in 20, 30 and 50 ml vials were inspected for inspected for signs of movement upon inversion by inverting a vial once. FIG. 1 is a bar graph that shows a number of vials containing lyophilized material that moved on inversion (shown as black bars) and number of vials containing lyophilized material that did not move upon inversion (shown as shaded bars). None of the Formulation I samples (the lyophilized pulmonary surfactant of the invention) moved on inversion while, all of the Formulation III samples and most of the Formulation II samples had moved. This test demonstrated that the lyophilized pulmonary surfactant of the invention has a superior position in the vials as compared to other samples.

Example 6

Proposed studies for stability and potency of APIs. The four APIs, KL4 (sinapultide), DPPC, POPG and Palmitic acid (PA), will be tested for integrity during selected time intervals, within 3 to 12 months storage at 25° C., 30° C. or 40° C. using HLPC. HPLC Parameters are presented in Table 6.

TABLE 6

| Chromatographic Conditions | |
|---|---|
| Instrument: | HPLC (Waters ALLIANCE ®, Waters Corp, Milford, MA) |
| Column: | Zorbax SB-C18 9 (Agilent Technologies, Santa Clara, CA) 150 × 4.6 mm, 3.5 micron particle size or equivalent column of the same dimensions and phase |
| Column Temperature: | 50° C. |
| Flow Rate: | 0.8 mL/minute |
| Detection: | Corona Plus Charged Aerosol Detector (CAD); ESA Corona Plus CAD |
| Inj. Volume: | At least 33 µL |
| Nitrogen ($N_2$): | Nitrogen Flow $N_2$ generator; set to 35 psi |
| Mobile Phase A: | Methanol:Water:Trifluoroacetic Acid (50.0:50.0:0.8, v/v/v) |
| Mobile Phase B: | Isopropanol:Methanol:Tetrahydrofuran:Trifluoroacetic Acid (70:15:15:0.8, v/v/v/v) |

Standards including each of the 4 APIs will be run to ascertain the pattern of the elution. Samples will be loaded on the column and the amounts of API will be calculated.

Example 7

Formulations I, II and III in 20, 30 and 50 ml vials were contemporaneously subjected to the BET testing. Notably, when Formulations I, II and III were shipped to Micromeritics via FEDEX, overnight, for the BET testing, Formulation III did not arrive intact, such that the cake had visibly collapsed and therefore, was unusable for testing. The material was shipped again using more secure packaging and still the samples in 50 ml vials (62-50) appeared collapsed. The test results for the sample 62-50 would not represent the true value.

BET testing was performed as follows: Analysis Adsorptive: Kr; Thermal Correction: Yes; Equilibration Interval: 10 s; Ambient Temperature: 22.00° C.; Automatic Degas: Yes. The results for the lyophilized material of the invention (Formulation I) are represented in Table 7. The results for Formulation II and III are represented in Table 8.

TABLE 7

| Parameters | Sample: 55-20 Formulation I, in 20 ml vials | Sample: 55-30 Formulation I, in 30 ml vials | Sample: 55-50 Formulation I, in 50 ml vials |
|---|---|---|---|
| Analysis Bath Temp | 77.155 K | 77.139 K | 77.110 K |
| Sample Mass | 0.3762 g | 0.4164 g | 0.1844 g |
| Warm Free Space Measured | 27.7288 cm$^3$ | 27.4722 cm$^3$ | 28.0054 cm$^3$ |
| Cold Free Space | 84.7298 cm$^3$ | 83.1997 cm$^3$ | 85.6894 cm$^3$ |
| Single point surface area | Measured at P/Po = 0.241772386: 2.4402 m$^2$/g | Measured at P/Po = 0.239917356: 2.5954 m$^2$/g | Measured at P/Po = 0.243909821: 1.9668 m$^2$/g |
| BET Surface Area | 3.4203 m$^2$/g ± 0.0239 m$^2$/g | 3.6868 ± 0.0194 m$^2$/g | 2.7108 ± 0.0243 m$^2$/g |
| Slope | 1.438722 ± 0.011382 g/cm$^3$ STP | 1.328621 ± 0.007963 g/cm$^3$ STP | 1.825983 ± 0.018413 g/cm$^3$ STP |

TABLE 7-continued

| Parameters | Sample: 55-20 Formulation I, in 20 ml vials | Sample: 55-30 Formulation I, in 30 ml vials | Sample: 55-50 Formulation I, in 50 ml vials |
|---|---|---|---|
| Y-Intercept | 0.211127 ± 0.001832 g/cm$^3$ STP | 0.201998 ± 0.001275 g/cm$^3$ STP | 0.255709 ± 0.003006 g/cm$^3$ STP |
| C | 7.814496 | 7.577384 | 8.140860 |
| Qm | 0.6061 cm$^3$/g STP | 0.6533 cm$^3$/g STP | 0.4804 cm$^3$/g STP |
| Correlation Coefficient | 0.9997498 | 0.9998563 | 0.9995935 |
| Molecular Cross-Sectional Area | 0.2100 nm$^2$ | 0.2100 nm$^2$ | 0.2100 nm$^2$ |

TABLE 8

| | Formulation II, 20 ml | Formulation II, 30 ml | Formulation II, 50 ml | Formulation III, 20 ml | Formulation III, 30 ml |
|---|---|---|---|---|---|
| BET Surface Area, m$^2$/g | 1.7613 ± 0.0167 m$^2$/g | 1.7663 ± 0.0193 m$^2$/g | 0.6462 ± 0.0069 m$^2$/g | 0.9445 ± 0.0061 m$^2$/g | 0.7282 ± 0.0032 m$^2$/g |
| Qm, cm$^3$/g STP | 0.3121 cm$^3$/g STP | 0.3130 cm$^3$/g STP | 0.1145 cm$^3$/g STP | 0.1674 cm$^3$/g STP | 0.1291 cm$^3$/g STP |

Specific surface area for Formulation I samples was in the range from about 3.7 m$^2$/g to about 2.7 m$^2$/g. Specific surface area for Formulation II samples was about 1.7 m$^2$/g. Specific surface area for Formulation III samples was in the range from about 0.6 m$^2$/g to about 0.9 m$^2$/g. Clearly, specific surface area for Formulation I samples was significantly larger than that of other samples.

Example 8

Formulation IV. When reconstituted with 10 ml of sterile water for injection, the lyophilized Formulation IV will provide the following concentration of APIs as shown in Table 9:

TABLE 9

| API | (mg/mL) |
|---|---|
| Sinapultide (KL$_4$) | 0.862 |
| Palmitic Acid | 4.05 |
| DPPC | 22.50 |
| POPG | 7.50 |

TABLE 10

Raw Materials for Formulation IV (8000 g Batch Size)

| Materials | Amount (mg) per gram of formulation | Amount (g) per batch |
|---|---|---|
| KL$_4$ (API) | 0.797 mg | 6.376 g |
| DPPC (API) | 17.99 mg | 143.9 g |
| POPG, Na (API) | 5.82 mg | 46.6 g |
| PA (API) | 3.11 mg | 24.88 g |
| 95% Ethanol | | 623.2 g |
| TRIS Buffer: | | |
| NaCl | 5.83 mg | 46.64 g |
| Tromethamine | 1.86 mg | 14.88 g |
| Water | | 6074 g |

Two batches were prepared in accordance with Table 10. Preparation of a pre-lyophilization mixture: the APIs were dissolved in 95% ethanol at 46° C.±1° C. to obtain a solution. The resultant solution was pressure filtered through a 0.22 micron 33 mm (PVDF) Millipore Millex GV cat. No SLGV033NS filter into stirring TRIS buffer solution at 45° C.±2° C. to produce a liposomal formulation with a final ethanol concentration of 7% (w/w). After cooling to a temperature below 30° C., the resultant liposomal formulation, i.e., the pre-lyophilization mixture, was transferred into 20, 30 and 50 mL borosilicate glass lyophilization vials at a fill volume of 13.7 g/vial using a peristaltic pump. The resultant lyophilized material was stored at 5° C.

Example 9

METHODS: Reconstitution. The requirements of a reconstituted solution are that there is no visible insoluble material and the solution is no less clear than the diluent after a predetermined amount of time. The volume for reconstitution may return the product to the same volume and concentration as the starting product for filling the bulk solution and may be the same volume intended for patient delivery in a clinical setting. Purified Water, USP as a diluent, at a volume of 10 ml was drawn up into a syringe. The diluent was then extruded into the center of the dried cake and the timer was started. The product was then inspected at approximately 5 second intervals in a light box to verify the absence of any insoluble material and clarity of the solution. The solution, once fully reconstituted, was characterized as being clear, colorless, hazy, opaque and/or cloudy. Particles, if present, were classified as being fine insolubles to coarse fibers. Undissolved excipients or API are noted as such.

pH Measurement—Reconstituted solutions (see above) were measured for pH per USP<791>, pH. Standardization with two or three pH buffers that bracket the expected sample range was performed prior to use. The pH buffers chosen were no greater than three pH units but, no less than two pH units apart (e.g., 4.01, 7.00, and 10.01). An ATC probe was used for automatic temperature compensation. A quantity of the sample solution sufficient to cover the pH probe sensor and any reference junction on the side of the probe was dispensed into a suitable container. The solution was gently swirled and then allowed to stand still and stabilize to a constant value over a period of at least 15 seconds, at which point, the displayed pH value was recorded.

Coulometric Karl Fischer Titration—Moisture testing followed widely accepted conventional methods outlined under USP<921>, Water Determination. The initial dried sample and container were weighed. A solvent extraction method with anhydrous methanol, special reagent, A.C.S was injected into the container used to suspend and dissolve the dried substance. The extraction volume of methanol used to cover the dried material was 13.0 ml to 13.7 ml for each study. The samples were then allowed to soak for a predefined time for extraction of the moisture in the product. An aliquot was then removed, the volume measured, then injected into the reaction vessel of the KF instrument. Upon reaching an end point of the titration, the results were reported. The KF instrument resolves water content to micrograms. The empty container was then weighed and the percentage moisture calculated for the initial container contents.

High Temperature Differential Scanning calorimetry (HT DSC)—Used as a means of determining the glass transition of solid materials, which provides useful information for evaluating the formulation and assessing behavior in the dried state. HT DSC follows the current USP<891>, Thermal Analysis and was performed using a Perkin Elmer DSC 7 interfaced to a TAC 7/7 Instrument Controller. Test parameters and data analysis were conducted using PYRIS software version 4.0 on a PC interface. Approximately 10-15 mg of solid material was placed in an aluminum sample pan with a crimped vented lid. Nitrogen, NF was used to purge the sample continuously at a flow rate of 20 ml/minute. The lyophilized material was warmed to evaluate the thermal behavior at higher temperatures. During warming, evolution or uptake of heat from the sample reflected the differences in energy as the sample underwent a thermal event. The scan data was recorded and graphed simultaneously using the Pyris® 4.0 software. Calculations identified the temperature at the onset and peak of a thermal event once the scan is complete. Based on the results of the scan, temperatures for such thermal events as a glass transition (Tg), crystallization, melting point (Tm), and associated heat of fusion, and/or specific heat of the dried finished product were determined utilizing this method.

RESULTS. The average residual moisture values of lyophilized samples of Formulation I were close to 0%. The average reconstitution time was between 8 and 10 seconds. High Temperature DSC scans performed on the material, at 2° C. per minute, indicated that a consistent significant endothermic peak was observed at a temperature between 49.0° C. and 51.0° C.

While the invention has been described in detail and with reference to specific examples thereof, it will be apparent to one skilled in the art that various changes and modifications can be made therein without departing from the spirit and scope thereof.

What is claimed is:

1. A process of making a lyophilized synthetic pulmonary surfactant having a reduced or eliminated cake levitation during the process, the process comprising:

providing to a lyophilizing chamber a pre-lyophilization mixture comprising dipalmitoyl phosphatidylcholine (DPPC), palmitoyloleoyl phosphatidylglycerol (POPG), palmitic acid and a synthetic peptide with SEQ ID NO:1 (KL4 polypeptide) dispersed in a solvent having an organic solvent in a range of between 3% (v/v) and 20% (v/v) of the total volume of the pre-lyophilization mixture with a remainder being water and/or buffer, wherein the pre-lyophilization mixture is filled in a container;

lowering a temperature inside the lyophilizing chamber to begin chilling and solidifying the pre-lyophilization mixture in a freezing phase; and conducting an annealing phase prior to a primary drying phase and thereby reducing or eliminating cake levitation in the lyophilized synthetic pulmonary surfactant wherein the lyophilized synthetic pulmonary surfactant has a specific surface area of at least 2.7 m$^2$/g.

2. The process of claim 1, the process comprising:

conducting the freezing phase in a process of lowering the temperature inside the lyophilizing chamber, wherein the pre-lyophilization mixture is chilled to a first temperature below −45° C. at a rate between 0.1 and 1.0° C./min and holding the pre-lyophilization mixture at the first temperature for a first period of time sufficient to solidify at least 76% of the solvent to form a first solidified mixture;

conducting the annealing phase and thereby reducing or eliminating cake levitation of the first solidified mixture, wherein the first solidified mixture is (i) heated to a second temperature selected to reduce or eliminate levitation of the first solidified mixture, (ii) held at the second temperature for a second period of time sufficient to reduce or eliminate levitation of the first solidified mixture, and (iii) chilled to a third temperature below −45° C. at a rate between 0.1 to 1.0° C./min to form a second solidified mixture, wherein the second solidified mixture is held at the third temperature for a third period of time sufficient to promote separation of unfrozen organic solvent from the second solidified mixture and thereby achieve a migration of the unfrozen organic solvent to an interface between the container and the second solidified mixture;

conducting a primary drying phase at a reduced pressure of 30 mT or higher, wherein the second solidified mixture is held at the fourth temperature for a fourth period of time sufficient to sublimate at least 10% of the organic solvent, followed by heating to a fourth temperature sufficient to keep the second solidified mixture from levitating in the container and retaining a structure established during the annealing phase, and further held at the fourth temperature for a fifth period of time sufficient to sublimate at least 85% of the solvent and thereby forming a third solidified mixture; and conducting a secondary drying phase at the reduced pressure for a sixth period of time sufficient to produce the lyophilized synthetic pulmonary surfactant having a residual solvent content of at most 2%.

3. The process of claim 2, wherein a ratio of the pre-lyophilization mixture's volume in the container to the container's volume is from about 28% to about 68%.

4. The process of claim 2, the process comprising:

providing the pre-lyophilization mixture wherein the organic solvent in the range from about 3% to about 15%.

5. The process of claim 2, the process comprising:

providing the pre-lyophilization mixture wherein the organic solvent in the range from about 5% to about 10%.

6. The process of claim 2, the process comprising:

providing the pre-lyophilization mixture wherein the organic solvent in the range from about 7% to about 10%.

7. The process of claim 2, the process comprising:

conducting the freezing phase, wherein the pre-lyophilization mixture is chilled to the first temperature −50° C.±3° C. at the rate between 0.1 and 1.0° C./min;

conducting the annealing phase, wherein the first solidified mixture is (i) heated to the second temperature of −22° C.±3° C. at a rate of 0.1 to 1.0° C./min, (ii) held at the second temperature for the second period of time between 4 and 8 hours, (iii) chilled to the third temperature of −50° C.±3° C. at a rate between 0.1 to 1.0°

C./min; and (iv) held at the third temperature for the third period of time for about 3 to 8 hours;

conducting the primary drying phase at a pressure of 40 mT±10 mT and temperature of −25° C.±3° C. ramped up from −50° C.±3° C., and further held at −25° C.±13° C. for 60 to 140 hours; and conducting the secondary drying phase at a pressure of 40 mT±10 mT and temperature of 25° C.±3° C. at 0.5° C./min ramped up from −25° C.±3° C. and held at 25° C.±3° C. for 4 to 10 hours.

8. The process of claim 2, wherein the specific surface area is in the range from about 3.7 $m^2/g$ to about 2.7 $m^2/g$.

9. The process of claim 2, wherein the lyophilized synthetic pulmonary surfactant has porosity above 40% by volume of a total area of the lyophilized synthetic pulmonary surfactant.

10. A lyophilized synthetic pulmonary surfactant composition comprising a synthetic peptide with SEQ ID NO:1 (KL4 polypeptide), dipalmitoyl phosphatidylcholine (DPPC), palmitoyloleoyl phosphatidylglycerol (POPG) and palmitic acid, wherein the lyophilized synthetic pulmonary surfactant composition has a specific surface area of at least 2.7 $m^2/g$.

11. The lyophilized synthetic pulmonary surfactant of claim 10, wherein the specific surface area is in the range from about 3.7 $m^2/g$ to about 2.7 $m^2/g$.

12. The lyophilized synthetic pulmonary surfactant of claim 10, wherein the lyophilized synthetic pulmonary surfactant has porosity above 40% by volume of a total area of the lyophilized synthetic pulmonary surfactant.

\* \* \* \* \*